United States Patent [19]

Ladisch et al.

[11] 4,345,973

[45] Aug. 24, 1982

[54] VAPOR PHASE DEHYDRATION OF AQUEOUS ALCOHOL MIXTURES

[75] Inventors: Michael R. Ladisch; George T. Tsao, both of West Lafayette, Ind.

[73] Assignee: Purdue Research Foundation, West LaFayette, Ind.

[21] Appl. No.: 181,244

[22] Filed: Aug. 25, 1980

[51] Int. Cl.³ .................. B01D 3/34; B01D 53/04; B01J 20/24; C07C 29/80

[52] U.S. Cl. ..................... 203/19; 203/41; 203/49; 203/DIG. 13; 55/62; 55/74; 568/916; 568/917; 252/426

[58] Field of Search ............ 203/19, 41, 49, 18, 203/DIG. 13; 568/916, 917; 252/426, 427; 55/62, 32, 74; 426/493, 494, 495; 435/161; 44/56, 53

[56] References Cited

U.S. PATENT DOCUMENTS

| | | | |
|---|---|---|---|
| 1,413,864 | 4/1922 | Mann | 568/917 |
| 1,493,756 | 5/1924 | La Bour | 203/90 |
| 1,667,426 | 4/1928 | Lourens | 55/74 |
| 1,833,717 | 11/1931 | Laird | 203/49 |
| 1,985,204 | 12/1934 | Derr et al. | 203/41 |
| 2,204,910 | 6/1940 | Randolph | 55/74 |
| 2,963,441 | 12/1960 | Dolian et al. | 55/74 |
| 3,122,486 | 2/1964 | Skarstrom | 203/41 |
| 3,132,079 | 5/1964 | Epperly et al. | 203/41 |
| 3,276,186 | 10/1966 | Hronas et al. | 55/74 |
| 3,806,609 | 4/1974 | Goblik et al. | 203/41 |

OTHER PUBLICATIONS

L. W. Carley: *How to Make Your Own Alcohol Fuels;* Aug. 1980, pp. 73-83.

*Primary Examiner*—Wilbur L. Bascomb, Jr.
*Attorney, Agent, or Firm*—Cushman, Darby & Cushman

[57] ABSTRACT

A method for dehydration and/or enrichment of aqueous alcohol mixtures wherein the mixtures in the vapor state are contacted with a dehydration agent which is composed of cellulose, caboxymethylcellulose, cornmeal, cracked corn, corn cobs, wheat straw, bagasse, starch, hemicellulose, wood chips, other grains, other agricultural residues or mixtures thereof.

10 Claims, 4 Drawing Figures

CONTROL CASES WITH EMPTY COLUMN

| | $T_{col}$ °C | ETHANOL IN DISTILLATE (%) |
|---|---|---|
| a. | 91.0 | 89.0 |
| b. | 94.0 | 87.2 |
| c. | 91.0 | NA |
| d. | 90.0 | 89.5 |
| e. | 79.5 | 92.5 |

VAPOR PHASE DEHYDRATION OF AQUEOUS ALCOHOL MIXTURES

BACKGROUND OF THE INVENTION

The present invention provides a way to dehydrate and enrich aqueous alcohol mixtures such as ethanol, in which the combustion energy of the ethanol product exceeds the energy needed to carry out the dehydration by a factor of 10. Drying of aqueous ethanol by materials such as cellulose, cornstarch, shelled corn, or corn (cellulosic) residue, results in a product that is up to 99.8 percent water-free.

Alcohols are made from either grains or biomass by first converting these materials to fermentable sugars. The sugars are then fermented, typically with yeast, to give a broth containing 6 to 12 percent ethanol along with small amounts of aldehydes, ketones, amyl alcohols (fusel oils), and methanol. The final step, distillation to water-free alcohol, consumes 50 to 80 percent of the energy used in a typical fermentation ethanol manufacturing process. The energy intensity of traditional distillation techniques is frequently cited in criticizing the potential of biomass-derived ethanol as a liquid fuel.

Thus, aside from its traditional use as a beverage or as a source of industrial alcohol, fermentation alcohol is also under study as a source of liquid fuel (i.e., anhydrous ethanol) which can be blended with gasoline in a 1:9 ratio. Since the sugars for the fermentation can be obtained from domestically available surplus grains and cellulosic residues, fermentation alcohol has the potential of significantly decreasing this country's dependence on imported oil.

Recovery of ethanol from the germentation broth is at least a three-step process: (i) distillation of dilute aqueous alcohol to its azeotrope (95.57 percent ethanol by weight), (ii) distillation using a third component—either an organic solvent or a strong salt solution to break up the azeotrope and remove the remaining water, and (iii) distillation to separate water from the third component so that it can be recycled. Trace constituents, including pentanol (fusel oil) and methanol, can be removed by additional distillation, but this is not necessary for ethanol to be blended for example with gasoline.

Analysis of the ethanol-water distillation, using the McCabe-Thiele method for analysis of fractionation columns, indicates the energy-sensitive regimes. Energy consumption greatly increases with decreasing ethanol concentration in the feed below 4 percent alcohol, since a disproportionately larger quantity of feed must be vaporized to obtain the same amount of product. Current fermentation technology results in a product containing 5 to 12 percent ethanol, so this energy problem is avoided. Most of the energy consumption occurs in distilling above 85 percent ethanol; With increasing alcohol product concentration (92.2 percent by weight alcohol), the rectifying operating line approaches the equilibrium line. Hence, more theoretical plates are required. To obtain a column with a reasonable number of plates (fewer than 40) for producing ethanol of higher purity, the slope of the rectifying line must be increased. This requires a higher reflux ratio and therefore more energy input.

By using the McCabe-Thiele method and constructing appropriate diagrams and using appropriate mass and energy balances, it can be shown that the energy content of 12 percent alcohol, distilled to 90 percent purity, is 11 times the energy needed for distillation. Above 90 percent, the energy ratio drops precipitously, and as the azeotrope is approached the distillation energy input approaches the ethanol energy output. Additional energy is required to carry out the other distillations to break the azeotrope.

The problem is to produce dehydrated ethanol in an energy-efficient manner, starting from 90 percent or lower concentrations. One solution is to use a non-distillation process. Aqueous ethanol can be dehydrated by preferential adsorption of water on adsorbents that are inexpensive and require relatively little energy for use or regeneration.

It is therefore a primary object of the present invention to provide an energy efficient means of dehydrating aqueous alcohol mixtures.

A further object of the present invention is to provide an efficient means of enriching dilute aqueous alcohol mixtures.

These and other objects of the present invention will become more apparent from the discussion which follows.

SUMMARY OF THE INVENTION

The present invention provides for a process for the dehydration of aqueous alcohol mixtures and separation of water therefrom which comprises contacting said mixtures while in the vapor state with a dehydration agent selected from the group consisting of cellulose, carboxymethylcellulose, cornmeal, cracked corn, corn cobs, wheat straw, bagasse, starch, hemicellulose, wood chips, other grains, other agricultural residues and mixtures thereof and recovering the alcohol with less than 5% water. Examples of other grains include wheat, barley, and rye. Examples of other agricultural residues include rice straw, grasses, and barley straw.

As used herein the phrase "aqueous alcohol mixtures" refers to those aqueous mixtures containing an alcohol which is capable of forming an azeotrope with water. Of particular interest are aqueous ethanol solutions which may contain from about 5 to 90% ethanol. Fermentation solutions containing from about 5 to 12 percent alcohol are of a special interest.

A further embodiment of the present invention provides for a means for the enrichment of aqueous alcohol mixtures which comprises passing an inert carrier gas stream through an aqueous alcohol mixture whereby a portion of said mixture is carried by said gas and thereafter passing the carrier gas stream containing aqueous alcohol vapor through a heated dehydration zone which contains a dehydration agent selected from the group consisting of cellulose, carboxymethylcellulose, cornmeal, cracked corn, corn cobs, wheat straw, bagasse, starch, hemicellulose, wood chips, other grains, other agricultural residues and mixtures thereof and recovering the alcohol with less than 5% water, and recovering the resulting enriched alcohol.

In such an enrichment scheme an inert carrier gas which will not react with either the mixture or dehydration agent may be used. Suitable gases include for example, air, nitrogen and carbon dioxide.

The dehydration bed must be heated to a temperature sufficient to volitilize the alcohol (i.e., greater than its dew point) and generally a temperature of about 90° C. is suitable.

The present invention also provides a different approach which is partial distillation followed by dehydration using a nondistillation technique. Research shows that dehydrated ethanol can be recovered from dilute alcohol at an energy input of about 1 Btu "in" per 10 Btu "out". Two approaches have potential for the energy efficient dehyration of alcohol. These are:

1. Partial distillation of 12% alcohol to a 70% to 90% aqueous product followed by vapor phase adsorption using adsorbents such as cellulose, cellulose derivative, cellulosic (corn) residue, or cracked corn (grain); and
2. Enrichment of 10% alcohol to 80% or higher alcohol by passing air or another suitable inert carrier gas through a 10% alcohol solution at 40° C., and then passing the gas stream containing the aqueous alcohol vapor through a column thermostated at 80° to 90° C. containing e.g. carboxymethyl (CM) cellulose.

These schemes thus circumvent some of the inefficiencies associated with distilling alcohol to the azeotrope point and then breaking the azeotrope formed between ethanol/water by subsequent distillations.

DETAILED DESCRIPTION OF THE INVENTION

Figure 1:
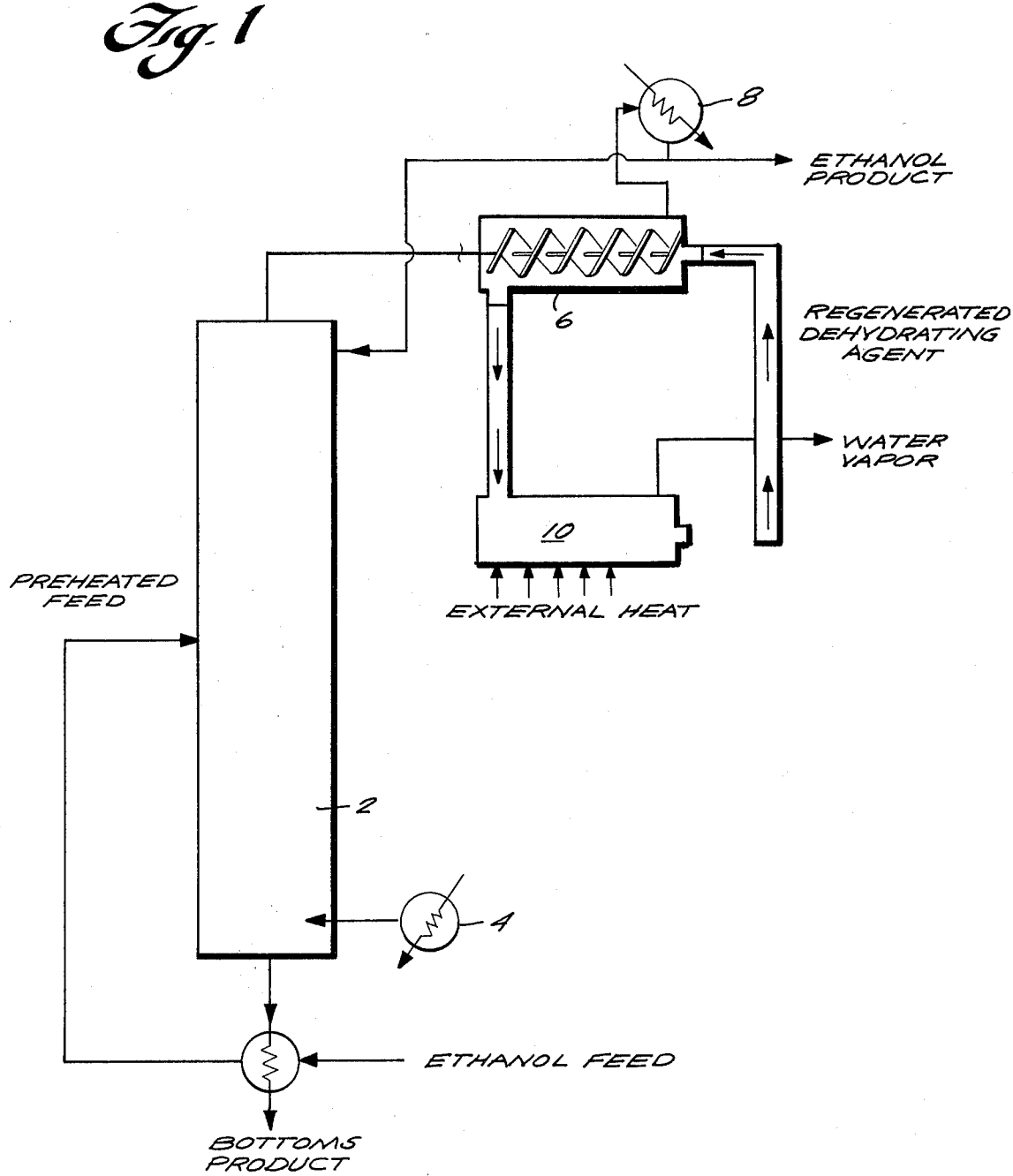
FIGS. 1, 2 and 3 depict various process configurations which may be used in accordance with the present invention.
Figure 2:
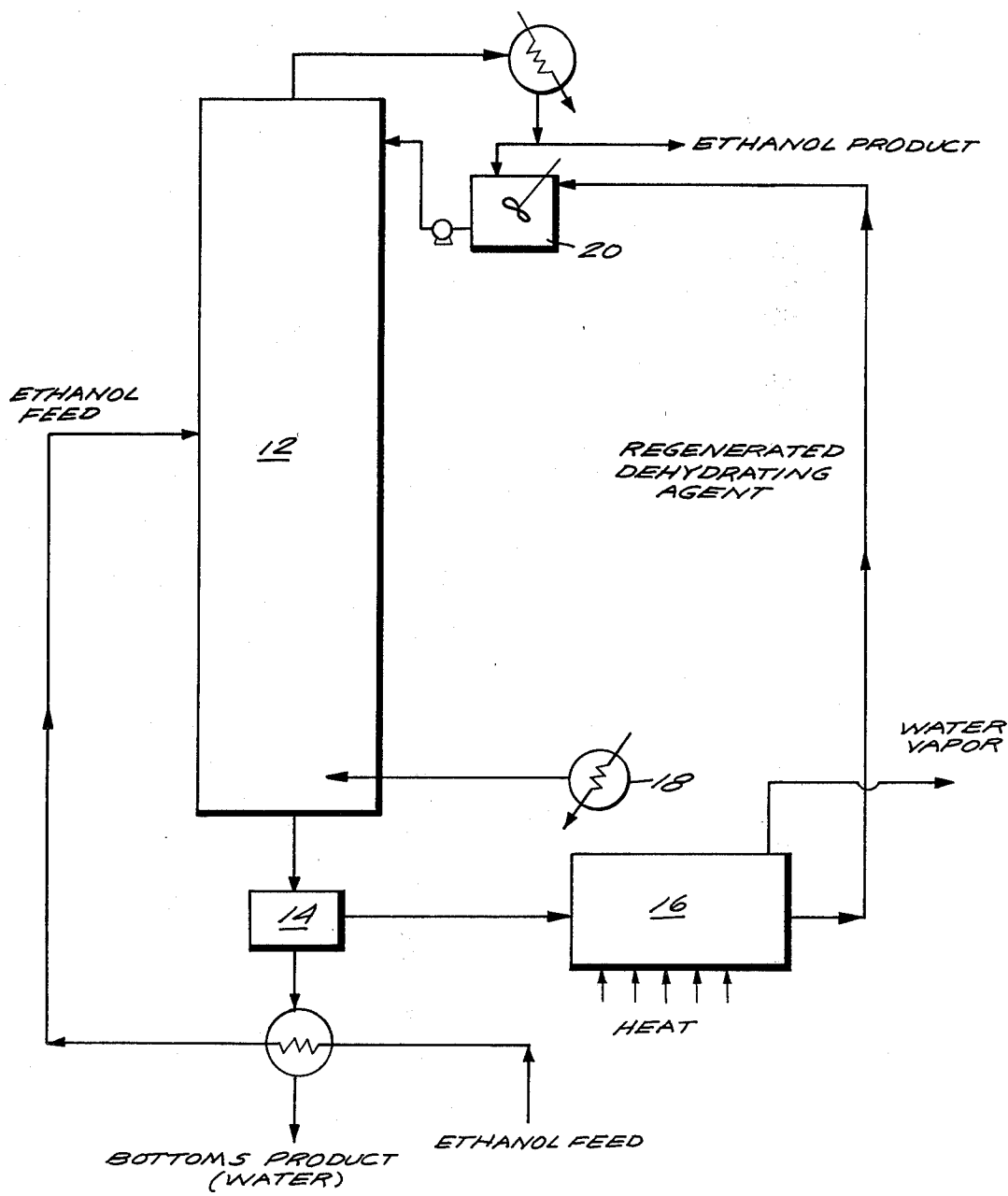
Figure 3:
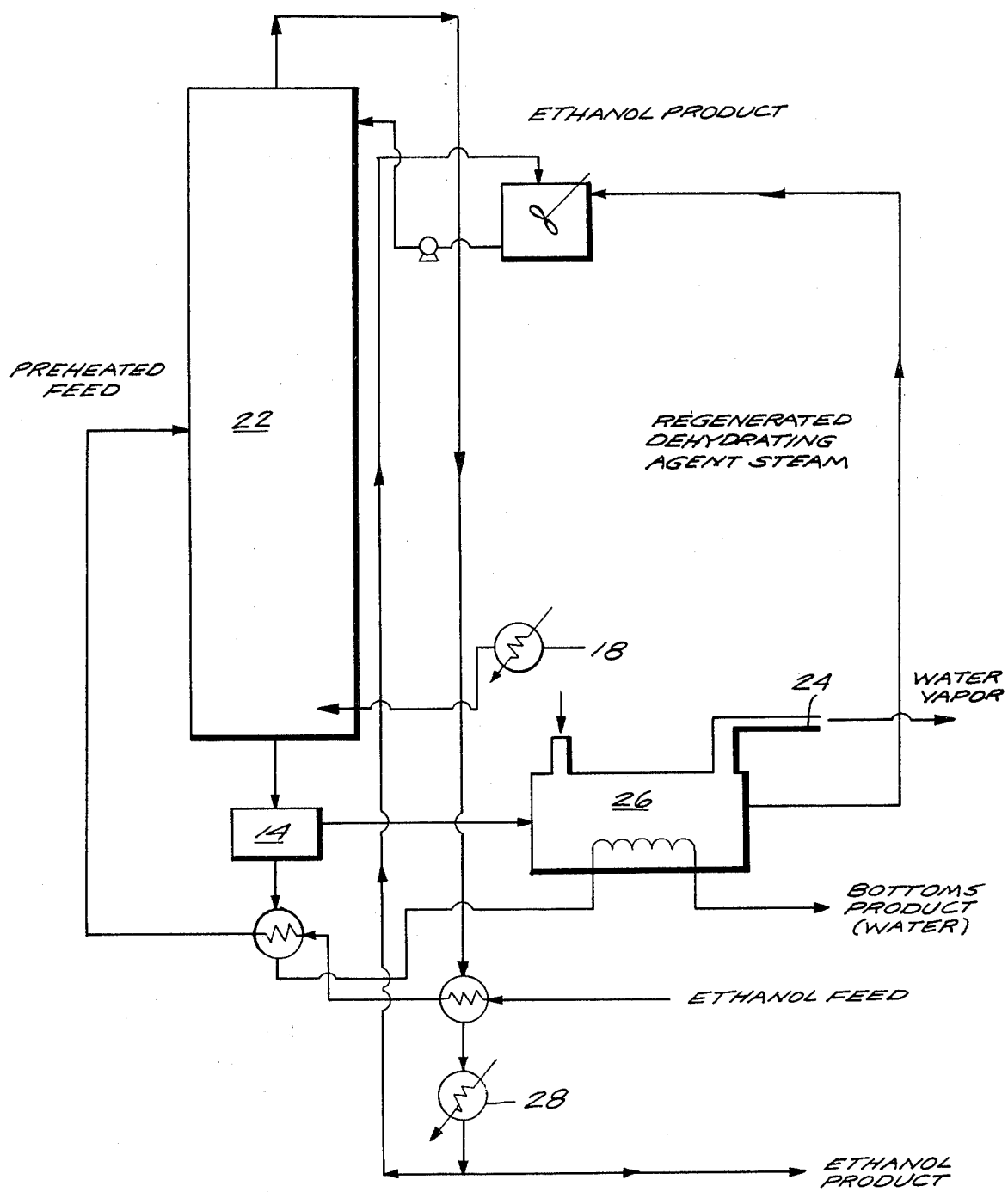

Possible process configurations which can be used with any of the dehydration agents of the present invention are illustrated in FIG. 1, FIG. 2, and FIG. 3.

Referring to FIG. 1, this configuration is a vaporsolid contact process. In this configuration, preheated feed enters the column at location shown. The feed is preheated by hot bottoms product. The feed which is at its boiling point before it enters the column, is introduced into the column (2) and then the distillation begins. Heat is provided to the column in the form of live steam or in the form of steam passing through a heat exchanger (4). The feed, once it enters the column, undergoes distillation. The enriched ethanol vapors pass through the rectifying section of the column (2) (the upper half of the column) and water flows eventually down the column through the stripping section (the bottom half of the column). The product from the bottom of the column is pure water. The product coming overhead from the top of the column is a water-ethanol mixture, which is 90% by weight ethanol or less. This vapor then passes through the auger unit (6) counter-current to solid dehydrating agent being transported through the unit by the action of the auger. On contact with the dehydrating agent in the auger unit, the water is absorbed or reacted with the dehydrating agent while the ethanol vapor passes through the unit and into a heat exchanger (8). The ethanol at this point is essentially water free. The ethanol is then condensed by cold water and a portion of this is recycled back to the distillation column. This is known as reflux. The rest of the ethanol is taken off as product.

The dehydrating agent once contacted with ethanol-water vapor soon is saturated to capacity. At this point the dehydrating agent passes from the auger unit (6) into a regeneration heater (10). In the regeneration heater external heat is used to heat up the dehydrating agent to drive off the water. Once regenerated, the dehydrating agent is again conveyed to the auger unit (6) and the cycle starts all over again.

The dehydration agents may generally be characterized as cellulosic or hemicellulosic or starchy in nature and preferably are selected from the grouping noted above.

A second process scheme is illustrated by FIG. 2, which is applicable to the dehydrating agents of the present invention. In this scheme the distillation column (12) is constructed from what is known as valve trays. These trays are slotted trays, which are capable of passing small amounts of solids without plugging up. In this case, slurry of the regenerated dehydrating agent would be mixed with anhydrous ethanol product and fed into the column (12). Aqueous ethanol vapors passing upward in the column would then contact this slurry in a counter-current manner. Dehydration action in this case would take place within the column, and the dehydrating agent which is soluble in neither alcohol nor water would eventually pass to the bottom of the column. At the bottom of the column, the solid would be separated from the liquid, by either filtration or a centrifuge (14), and then it would pass through a regeneration heater (16). In the regeneration heater (16), the solid material would be regenerated and then recycled to the mixed once more with the anhydrous ethanol produce.

The bottom product from the column would then be water and slurry. The slurry would be separated as mentioned previously in a solid-liquid separation device (14), giving two streams, one a solid and the other a liquid—the water. The water, of course, would be hot and would be used to preheat the ethanol feed to the column (12), to its bubble point. Heat through this column would either be live steam or would be steam passed through a heat exchanger (8). The overhead product coming from the column would be dehydrated alcohol and would pass through a condenser (20) where cold water would be used to condense the vapors. A certain portion of the ethanol would be used to make a slurry of the regenerated dehydrating agent and ethanol. The remaining ethanol would then be drawn off as product as shown in FIG. 2.

Another possible process design is shown in FIG. 3. This particular design is a modification of the process shown in FIG. 2. In this design, the heat of regeneration for the dehydrating agent is supplied by the hot water, coming out of the bottom of the column (22). In this case it is assumed that the dehydrating agent will be regenerated by a fairly low level temperature, on the order of 90° C. This temperature would be feasible for a material such as cellulose, starch, or cellulosic residue. In this case there would be a forced exhaust (24), in other words, a slight vacuum would be drawn through the regeneration heater (26) by a forced exhaust fan system. The various steps in the process are essentially the same except that the bottoms product is used to only partially preheat the incoming ethanol feed and the rest of the heat is used for the regeneration heater (26). The ethanol feed is used in this case to condense the overhead vapor product and at the same time the feed itself is heated up. Probably in this case, only partial condensation of the overhead ethanol product would be achieved, so a secondary heat exchanger (28) with cold water would be needed to complete the condensation.

Although the water-adsorbing properties of cellulose and starch are known, preferential adsorption of water in the presence of ethanol was unexpected. Furthermore, the energy balance is more favorable than that obtained with CaO. For example, the heat of wetting of cellulose, on the order of 50 Btu's per pound, is less than the heat of reaction of CaO. The total energy requirement with cellulose as the dehydrating agent is 1235 Btu's per pound of alcohol: 1050 Btu's per pound for distillation (from 12 to 84.8 percent) and 185 Btu's per pound for cellulose dehydration. Hence, ten times more (combustible) energy is obtained than is used in obtaining the product.

The following examples are offered to more fully illustrate the invention, but are not to be construed as limiting the scope thereof.

EXAMPLE ONE

Ethanol-water vapor was passed through a 20-ml condenser tube (heated at 88° to 95° C.) filled with calcium oxide (CaO). The vapor coming from the tube was condensed, collected, and then analyzed for water content by the Karl-Fischer (KF) water analysis procedure. Vapor with a starting composition of 89 percent ethanol and 11 percent water was successfully dehydrated in this way to give a product with 99+ percent ethanol. This result is not surprising since CaO is known to react with water [$CaO + H_2O$ $Ca(OH)_2 + 2527$ Btu's per pound of water] and would not be expected to react with ethanol.

TABLE 1

Comparison of alcohol-dehydrating agents.

| Material | Ethanol (%) | |
|---|---|---|
| | Starting | Dehydrated |
| Cornstarch | 73.7 | 99.0 |
| Sucrose | 72.5 | 90.7 |
| Corn | 77.0 | 97.7 |
| Avicel (microcrystalline cellulose) | 88.9 | 98.6 |
| Whatman CF-11 cellulose | 88.8 | 96.4 |
| Buckeye CM cellulose | 84.8 | 99.8 |
| Corn residue | 85.2 | 92.0 |

EXAMPLE TWO

Figure 4:
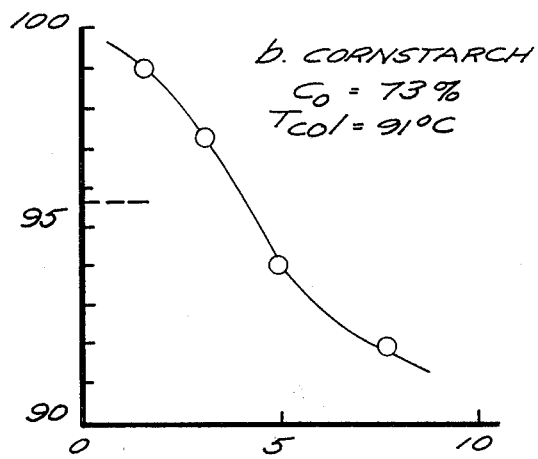
FIG. 4 is a series of graphs summarizing qualitative properties of selected dehydrating agents.
Figure 4:
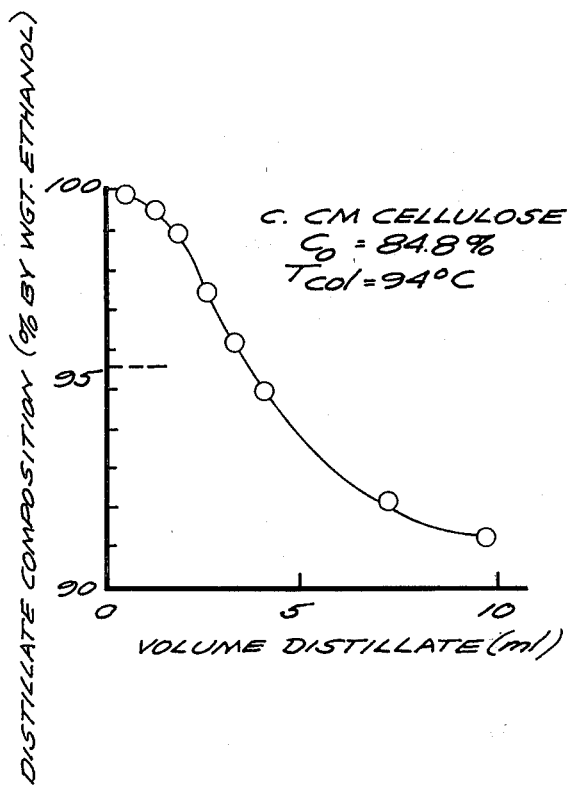
Figure 4:
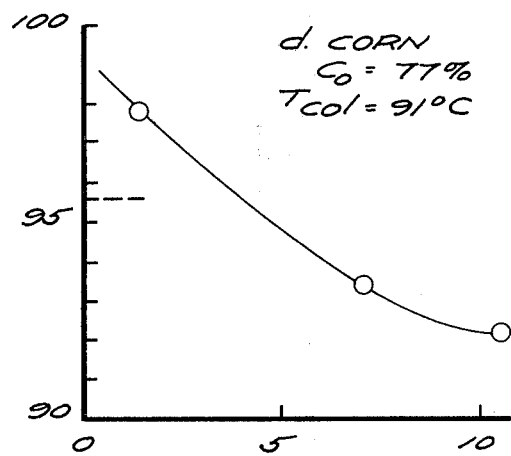
Figure 4:
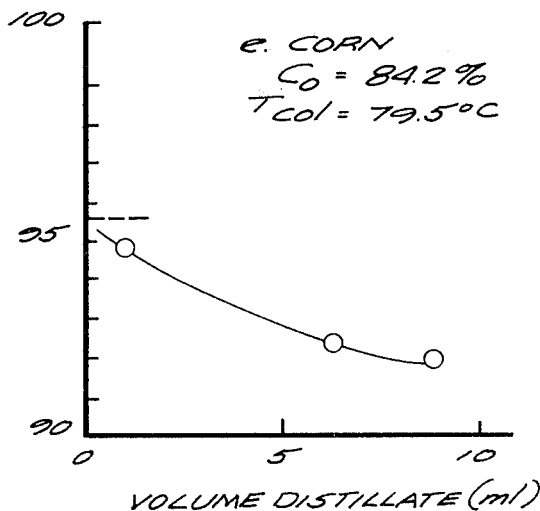

Quantitative properties of selected dehydrating agents are summarized in FIG. 4. These materials were heated before use: cornstarch (Argo Division, Corn Products Co.) at 90° C., CM cellulose (type CLD, Buckeye Co.) at 110° C., Avicell and CF-11 at 60° C. in a vacuum (30 inch-Hg), and corn (shelled and cracked) at 90° C. Aqueous ethanol at a concentration of $C_o$ percent by weight was put into an insulated 300-ml round-bottom flask heated by an electric mantle. A jacketed column, 20 ml in volume, was placed vertically in the flask neck. The column was maintained at temperature $T_{col}$ by using a Haake model FE circulating-water bath. A receiver, placed immediately at the outlet of the column, condensed and collected the vapor from the column. All non-heated parts of the apparatus were well insulated.

Before each run, ethanol was placed in the flask and the entire system was heated to steady state. After the heating, and before filling the column with dehydrating agent, control values were obtained. "Distillate" as well as the contents of the flask ("bottoms" at $C_o$) were sampled and analyzed by the KF procedure for water. The results are indicated in FIG. 4. Preheated dehydrating agent was then quickly placed in the column. Weights of materials were cornstarch, 7.3 g; CM cellulose, 3.4 g; and corn, 7.5 g.

The enhancement of the ethanol concentration is due to dehydration and not solely to additional fractionation effects of the packing material in the column. Passage of ethanol vapors over starch (FIG. 4b) gives a dramatic dehydration, yielding 99 percent ethanol from a 73 percent starting concentration. Similarly, cracked corn kernels also dehydrate alcohol (FIG. 4d). This result indicates the potential use of grain to dehydrate alcohol before the grain is converted (by wet processing) to alcohol in a grain alcohol plant. The effectiveness of CM cellulose (FIG. 4c) suggests that other modified carbohydrate polymers such as superadsorbent starch ("superslurper")(10) might have the potential to dehydrate alcohol.

Column temperature has a significant effect on dehydration. At $T_{col}=91°$ C., corn readily dehydrates alcohol. At $T_{col}=79.5°$ C. the dehydration capacity is diminished, even though the starting ethanol concentration is 7 percent higher. Similar phenomena were observed for other dehydrating agents. The vapor contact times are short: on the order of 4 seconds for NaOH, 14 seconds for starch, 28 seconds for CM cellulose, and 5 seconds for corn.

EXAMPLE THREE

With reference to the configuration of FIG. 3, a preheated feed containing 10 pounds of ethanol and 100 pounds of water (i.e., 10% ethanol) is introduced to the column (22). Assuming that 89 pounds of water passes to the bottom of the column, then only 1 pound of water will be absorbed by the dehydrating agent. The energy required to regenerate this amount of dehydrating agent will be approximately 1,000 Btu's. This amount of energy would be provided by the water which is coming out of the bottom of the column, if the water experienced a 12° F. temperature drop. In other words, the water leaving the bottom of the column is a saturated liquid at approximately 100° C. or 212° F. In order for this water to provide the necessary heat, it would have to undergo a temperature drop from 212° F. to 200° F.

EXAMPLE FOUR

A series of experiments was run with CM-cellulose using a different approach. Here air (line pressure=15 to 20 psig) at 40° C., was bubbled through a flask, also at 40° C., containing 10% to 12% ethanol in water. The gas then swept through a column packed with CM-cellulose at 91° C. The alcohol stream exiting from the column was condensed at room temperature followed by condensing on ice in a collection flask. The ethanol collected was 70% pure (the balance, 30%, being water). This result is quite impressive considering that the same procedure performed with an empty column gave only 16% alcohol and with a column tightly packed with glass wool gave 36% to 39% alcohol. Passage of vapor (obtained by boiling 10% ethanol) over the CM-cellulose column gave 80% product.

As an alternative example, $CO_2$ resulting from the fermentation could be collected and compressed to 10 to 20 psig. The gas could then be bubbled through the fermentation broth and swept over the packed bed. After the alcohol vapors are condensed a portion of the $CO_2$ gas could be collected for reuse. The primary energy costs here would be due to compression costs and due to the sizable heat load needed to keep the column at 90° C.

Another test was run using corn residue as a packing material. The residue was dried, packed, and operated at the same conditions as described previously. A remarkable dehydration effect was again observed. Alcohol of 80.7% ethanol composition was dehydrated to 95%. Although further improvements in capacity are desirable, these results nonetheless indicater the potential of using the incoming "feedstock" to a biomass refinery as dehydrating agents.

An even more dramatic dehydration effect is obtained with cracked corn kernels which were dried at 110° C. for several hours, packed, and operated as before. A product of up to 99% alcohol starting from 81.7% alcohol was obtained when the 81.7% mixture ws vaporized and passed over the column. The results indicate that corn residue has significant capacity. The weight of kernels packed in the column was 8.6 grams. This quantity of corn is sufficient to produce 4 mls of 81.7% ethanol. The data also indicates that dehydration capacity is not decreased if corn is dried and used over again one time, as was done to dehydrate 90.6% ethanol. These results also indicate that the capacity of the corn residue is within the range needed if incoming corn were to be used to dehydrate alcohol prior to being processed to give alcohol.

From a practical point of view, the dehydrating agents of this invention are attractive since they are readily regenerated by heating and can be recycled. Furthermore, cellulosic materials, corn residue, and cornstarch are materials that would be available, or could be generated internally, in plants converting cellulosic residues or grains to alcohol. Another advantage of using organic rather than inorganic dehydrating agents is that the temperature of regeneration is lower for starch or cellulosics (60° to 110° C.) than it is for CaO (160° to 170° C.). Hence, lower temperature energy, not usable elsewhere in an alcohol production facility, could be utilized for regenerating a dehydrating agent such as cellulose or starch. This might result in further energy economy.

The invention having been thus described, it is to be understood that same may comprise, consist or consist essentially of the hereinabove recited materials and steps.

What is claimed is:

1. A process for the dehydration of aqueous alcohol mixtures and separation of water therefrom which comprises contacting said mixtures while in the vapor state with a dehydration agent selected from the group consisting of cellulose, carboxymethylcellulose, cornmeal, cracked corn, corn cobs, wheat straw, bagasse, starch, hemicellulose, wood chips, other grains, other agricultural residues and mixtures thereof and recovering the alcohol with less than 5% water.

2. The process of claim 1 wherein said alcohol is ethanol.

3. The process of claim 2 wherein the aqueous alcohol mixtures contain from 5 to 90% of ethanol.

4. The process according to claim 2 wherein said aqueous alcohol mixture is a fermentation product containing from about 5 to 12 percent ethanol.

5. A process for the dehydration of aqueous ethanol mixtures and separation of ethanol therefrom which comprises heating said mixtures to produce a vapor of aqueous ethanol, contacting said vapor of aqueous ethanol with a dehydration agent selected from the group consisting of cellulose, carboxymethylcellulose, cornmeal, cracked corn, corn cobs, wheat straw, bagasse, starch, hemicellulose, wood chips, other grains, other agricultural residues and mixtures thereof and recovering the alcohol with less than 5% water.

6. A process for the enrichment of aqueous alcohol mixtures which comprises passing an inert carrier gas stream through an aqueous alcohol mixture whereby a portion of said mixture is carried by said gas and thereafter passing the carrier gas stream containing aqueous alcohol vapor through a heated dehydration zone which contains a dehydration agent selected from the group consisting of cellulose, carboxymethylcellulose, cornmeal, cracked corn, corn cobs, wheat straw, bagasse, starch, hemicellulose, wood chips, other grains, other agricultural residues and mixtures thereof and recovering the alcohol with less than 5% water, and recovering the resulting enriched alcohol.

7. A process according to claim 6 wherein said alcohol is ethanol.

8. A process according to claim 6 or 7 wherein said inert carrier gas is selected from the group consisting of air, nitrogen and carbon dioxide.

9. A process according to claim 8 wherein said dehydration zone is heated to a temperature above the dew point of said alcohol.

10. A process according to claim 9 wherein the zone is heated to about 90° C.

* * * * *